United States Patent [19]

Förster et al.

[11] Patent Number: 4,540,430

[45] Date of Patent: Sep. 10, 1985

[54] HERBICIDALLY ACTIVE NOVEL SUBSTITUTED 3-TRICHLOROMETHYL-1,2,4-THIADIAZOL-5-YL-OXYACETAMIDES

[75] Inventors: Heinz Förster; Hans-Joachim Diehr; Jörg Stetter, all of Wuppertal; Ludwig Eue, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 515,082

[22] Filed: Jul. 18, 1983

[30] Foreign Application Priority Data

Jul. 28, 1982 [DE] Fed. Rep. of Germany ....... 3228131

[51] Int. Cl.³ .................... C07D 285/08; A01N 43/82
[52] U.S. Cl. ................................. 71/90; 260/239 BF; 544/134; 546/146; 546/164; 546/165; 546/208; 548/129
[58] Field of Search ................ 548/129; 546/146, 164, 546/165, 208; 544/134; 260/239 BF; 71/90

[56] References Cited

U.S. PATENT DOCUMENTS 3,260,725  7/1966  Schroeder ........................... 548/129
4,204,857  5/1980  Rothgery ............................ 548/129
4,408,055  10/1983  Forster ................................ 548/129

FOREIGN PATENT DOCUMENTS 3038036  5/1982  Fed. Rep. of Germany ...... 548/129
802020  7/1981  South Africa ..................... 548/129

Primary Examiner—Robert Gerstl
Attorney, Agent, or Firm—Sprung Horn Kramer & Woods

[57] ABSTRACT

A substituted 3-trichloromethyl-1,2,4-thiadiazol-5-yl-oxyacetamide of the formula

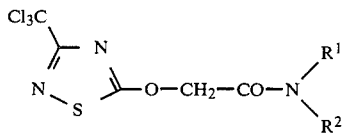

in which R¹ and R² are identical or different and individually represent optionally substituted alkyl, alkenyl, alkinyl, alkoxy, aralkyl, cycloalkyl, cycloalkenyl, aryl or a nitrogen-containing heterocyclic radical, or, together with the nitrogen atom to which they are bonded, form an optionally substituted, optionally partially unsaturated and optionally benzo-fused monocyclic or bicyclic structure which optionally contains further heteroatoms, which possesses herbicidal activity.

11 Claims, No Drawings

HERBICIDALLY ACTIVE NOVEL SUBSTITUTED 3-TRICHLOROMETHYL-1,2,4-THIADIAZOL-5-YL-OXYACETAMIDES

The invention relates to new substituted 3-trichloromethyl-1,2,4-thiadiazol-5-yl-oxyacetamides, a process for their preparation and their use as herbicides.

It is already known that certain azolyloxycarboxamides can be used as herbicides (see, for example, DE-OS (German Published Specifications) Nos. 2,822,155 and 2,903,966, European Pat. No. 5,501, DE-OS (German Published Specifications) Nos. 2,914,003 and 3,004,326, and European Pat. No. 18,497), for example 2-(benzothiazol-2-yl)-oxyacetic acid N-methylanilide. This active compound is primarily employed for combating gramineae; however, this compound is not always completely effective against some important grasses, and especially in relatively low doses.

New substituted 3-trichloromethyl-1,2,4-thiadiazol-5-yl-oxyacetamides of the formula

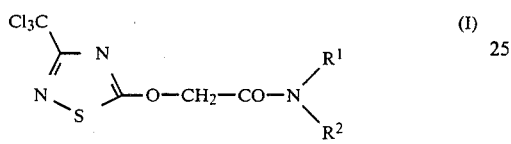

in which
R$^1$ and R$^2$ are identical or different and individually represent optionally substituted alkyl, alkenyl, alkinyl, alkoxy, aralkyl, cycloalkyl, cycloalkenyl, aryl or a nitrogen-containing heterocyclic radical, or, together with the nitrogen atom to which they are bonded, form an optionally substituted, optionally partially unsaturated and optionally benzo-fused monocyclic or bicyclic structure which optionally contains further hetero atoms, have now been found.

The new compounds of the formula (I) are obtained when hydroxyacetamides of the formula

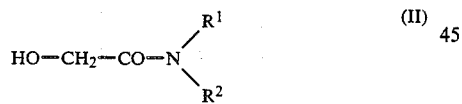

in which
R$^1$ and R$^2$ have the meaning given above, are reacted with 5-chloro-3-trichloromethyl-1,2,4-thiadiazole of the formula

in the presence of an acid acceptor and, if appropriate, using a diluent.

The new substituted 3-trichloromethyl-1,2,4-thiadiazol-5-yl-oxyacetamides of the formula (I) are distinguished by powerful herbicidal activity.

Surprisingly, the active compounds according to the invention, of the formula (I), show, against a number of important grasses, a clearly better activity than the previously known 2-(benzothiazol-2-yl)-oxyacetic acid N-methylanilide. The new active compounds thus represent an enrichment of the art.

The invention preferably relates to 3-trichloromethyl-1,2,4-thiadiazol-5-yl-oxyacetamides of the formula (I) in which
R$^1$ and R$^2$, which can be identical or different, individually represent alkyl, cyanoalkyl, alkoxyalkyl, alkylthioalkyl, alkenyl, alkinyl or alkoxy, each having up to 10 C atoms, cycloalkyl or cycloalkenyl, each having up to 12 C atoms, aralkyl which has 1 or 2 carbon atoms in the alkyl part and 6 or 10 carbon atoms in the aryl part, and is optionally substituted by halogen, or represents aryl having 6 or 10 carbon atoms, it being possible for the aryl radical to be substituted by 1 to 3 halogen atoms, 1 to 3 alkyl or halogenoalkyl groups each having 1 to 4 carbon atoms, nitro, cyano or alkoxy having 1 to 4 carbon atoms, or wherein
the radicals R$^1$ and R$^2$, together with the nitrogen atom to which they are bonded, form an optionally partially unsaturated and/or benzofused monocyclic or bicyclic structure which has up to 15 carbon atoms and is optionally substituted by 1 to 3 alkyl groups, each having 1 to 5 carbon atoms, or wherein
the radicals R$^1$ and R$^2$, together with the nitrogen atom to which they are bonded, form a saturated monocyclic structure which has up to 5 carbon atoms, is optionally substituted by 1 to 3 alkyl groups, each having 1 to 5 carbon atoms, and optionally contains a further nitrogen atom, oxygen atom or sulphur atom.

The invention relates, in particular, to compounds of the formula (I) in which
R$^1$ represents C$_1$–C$_5$-alkyl, cyanoethyl, C$_1$–C$_4$-alkoxy-ethyl, allyl, propargyl, 1-methyl-propargyl or 1,1-dimethyl-propargyl and R$^2$ represents C$_1$–C$_5$-alkyl, C$_1$–C$_5$-alkoxy, cyanoethyl, C$_1$–C$_4$-alkoxy-ethyl, allyl, propargyl, 1-methyl-propargyl, 1,1-dimethylpropargyl, cyclopentyl, cyclohexyl, 3,4,6-trimethyl-cyclohexene-1-yl, benzyl, naphthyl or phenyl, which is optionally substituted by 1 to 3 radicals (methyl, chlorine, fluorine, trifluoromethyl, methoxy, methylthio, trifluoromethoxy and/or trifluoromethylthio), or wherein
the radicals R$^1$ and R$^2$, together with the nitrogen atom to which they are bonded, represent pyrrolidyl, monoalkyl- or dialkyl-pyrrolidyl having 1 to 3 carbon atoms per alkyl group, morpholinyl, or dialkylmorpholinyl having 1 to 3 carbon atoms per alkyl group, piperidyl, monoalkyl-, dialkyl- or trialkylpiperidyl having 1 to 3 carbon atoms per alkyl group, perhydroazepinyl (hexamethyleneimino radical), the heptamethyleneimino radical, 1,2,3,4-tetrahydroindolyl, monoalkyl- or dialkyltetrahydroindolyl having up to 3 carbon atoms per alkyl group, perhydroindolyl, monoalkyl- or dialkylperhydroindolyl having 1 to 3 carbon atoms per alkyl group, 1,2,3,4-tetrahydroquinolyl or 1,2,3,4-tetrahydro-iso-quinolyl, monoalkyl- or dialkyl-1,2,3,4-tetrahydroquinolyl or -iso-quinolyl having 1 to 3 carbon atoms per alkyl group, perhydroquinolyl or perhydro-iso-quinolyl, monoalkyl- or dialkyl-perhydroquinolyl or -perhydroisoquinolyl having 1 to 3 carbon atoms per alkyl group.

Out of this group of compounds, there are of special interest those compounds of formula (I), wherein $R^1$ represents a branched or unbranched alkyl radical with 1 to 5 carbon atoms, and $R^2$ represents a branched or unbranched alkoxy radical with 1 to 5 carbon atoms.

If 5-chloro-3-trichloromethyl-1,2,4-thiadiazole and, for example, hydroxyacetic acid N-methylanilide are used as starting materials, the course of the reaction in the process according to the invention can be represented by the following equation:

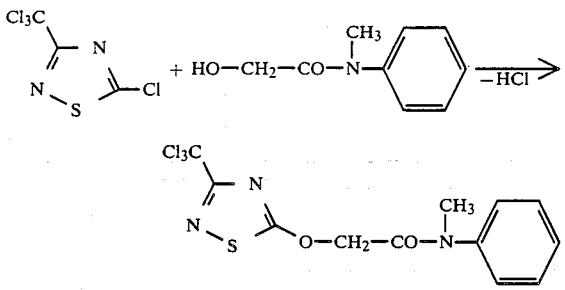

Formula (II) gives the definition of the hydroxyacetamides to be used as starting materials. In this formula, $R^1$ and $R^2$ preferably or particularly represent those radicals which have already been mentioned within the scope of the definitions of the substituents for formula (I) as being preferred or particularly preferred.

The following may be mentioned as examples of starting materials of the formula (II):

hydroxyacetic acid dimethylamide, diethylamide, di-n-propylamide, di-iso-propylamide, N-methyl-N-iso-propylamide, N-methyl-N-isobutyl-amide, N-methyl-N-sec.-butylamide, N-propyl-N-sec.-butyl-amide, N-methyl-N-(2-cyanoethyl)-amide, di(2-methoxy-ethyl)-amide, di-allyl-amide, N-methyl-N-propargyl-amide, N-methyl-N-(1-methyl-propargyl)-amide, di-propargyl-amide, N-methyl-N-cyclopentyl-amide, N-methyl-N-cyclohexyl-amide, N-methyl-N-(2-nitro-phenyl)-, N-methyl-N-(3-nitro-phenyl)- und N-methyl-N-(4-nitro-phenyl)amide, N-methyl-N-(2-chloro-phenyl)-, N-methyl-N-(3-chloro-phenyl)- and N-methyl-N-(4-chloro-phenyl)-amide, N-methyl-N-(3-nitro-6-methylphenyl)-amide, N-ethyl-anilide, N-ethyl-N-(2-nitro-phenyl)-, N-ethyl-(3-nitro-phenyl)- and N-ethyl-N-(4-nitro-phenyl)-amide, N-ethyl-N-(2-chloro-phenyl)-, N-ethyl-N-(3-chloro-phenyl)- and N-ethyl-N-(4-chloro-phenyl)-amide, N-ethyl-N-(3-nitro-6-methyl-phenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methyl-phenyl)- and N-propyl-N-(4-methyl-phenyl)-amide, N-propyl-N-(3-nitro-6-methyl-phenyl)-amide, N-butyl-anilide, N-methyl-N-naphth-1-ylamide, N-methyl-N-naphth-2-ylamide, N-ethyl-N-naphth-1-ylamide, N-ethyl-N-naphth-2-ylamide, N-methyl-N-benzylamide, N-ethyl-N-benzylamide, N-propyl-N-benzylamide, N-butyl-N-benzylamide, pyrrolidide, 1-methyl-pyrrolidide, morpholide, piperidide, 2-methyl-piperidide, 2-methyl-piperidide, 4-methyl-piperidide, 2,4-dimethyl-piperidide, 3,5-dimethyl-piperidide, 3,5-diethylpiperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2,-ethyl-4-methyl-piperidide, 2-methyl-5-ethyl-piperidide, 2-ethyl-5-methyl-piperidide, 2-methyl-6-ethyl-piperidide, 1,2,3,4-tetrahydroindolide, 2-methyl-1,2,3,4-tetrahydroindolide, perhydroindolide, 2L -methyl-perhydroindolide, 2,2-dimethyl-perhydroindolide, 2-methyl-1,2,3,4-tetrahydroquinolide, perhydroquinolide, 2-methyl-perhydroquinolide, 1,2,3,4-tetrahydroisoquinolide and perhydroisoquinolide; and also N-methyl-N-(2-methylthio-phenyl)-, N-methyl-N-(3-methylthio-phenyl)- and N-methyl-N-(4-methylthio-phenyl)-amide, N-methyl-N-(2-fluorophenyl)-, N-methyl-N-(3-fluorophenyl)- and N-methyl-N-(4-fluorophenyl)-amide; N-methyl-N-(2-trifluoromethylphenyl)-, N-methyl-N-(3-trifluoromethylphenyl)- and N-methyl-N-(4-trifluoromethylphenyl)-amide; N-methyl-N-(2-trifluoromethoxyphenyl)-, N-methyl-N-(3-trifluoromethoxyphenyl)- and N-methyl-N-(4-trifluoromethoxyphenyl)-amide; and N-methyl-N-(2-trifluoroethylphenyl)-amide.

Some of the hydroxy-carboxamides of the formula (II) are known (see U.S. Pat. No. 3,399,988; and DE-OS (German Published Specifications) Nos. 2,201,432 and 2,647,481). They can be prepared, as shown in the equation below, using chloroacetyl chloride as a starting material:

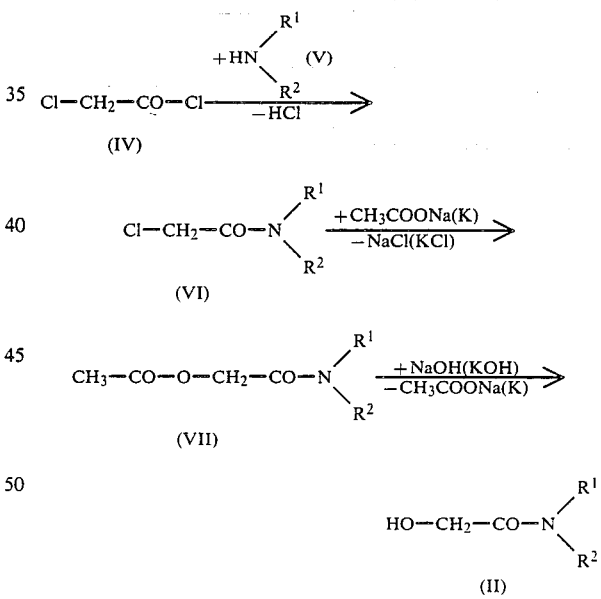

For this purpose, the chloroacetyl chloride which is known from the literature and is of the formula (IV) is first converted to the corresponding chloroacetamides of the formula (VI), using amines of the formula (V), wherein $R^1$ and $R^2$ have the meanings given above, if appropriate in the presence of an acid-binding agent, such as, for example, triethylamine, and, if appropriate, using an inert diluent, such as, for example, 1,2-dichloroethane, at temperatures between $-20°$ and $100°$ C., preferably between $-10°$ and $50°$ C. These products are worked up according to customary methods, by washing with water, drying the organic phase and distilling off the solvent.

The compounds of the formula (VI) are reacted with sodium acetate or potassium acetate, if appropriate using a diluent, such as, for example, acetic acid or dimethylsulphoxide, at temperatures between 20° and 150° C., preferably between 50° and 120° C., to give the corresponding acetoxy-acetamides of the formula (VII). If the products are obtained in this process in crystalline form, they are isolated by filtering them off under suction. Otherwise, working up is effected according to customary methods, for example by distilling off the solvent in vacuo, taking up the residue in methylene chloride, washing the solution with water and distilling off the solvent.

By reaction with aqueous-alcoholic sodium hydroxide solution or potassium hydroxide solution at temperatures between 0° and 100° C., preferably between 10° and 50° C., the compounds of the formula (VII) can be de-acylated to give the compounds of the formula (II). To isolate the products, the solvents are distilled off in vacuo, the residue is extracted with organic solvent, such as, for example, methylene chloride or ethyl acetate, the solution is dried and the solvent is distilled off.

Formula (III) gives a definition of the 5-chloro-3-trichloromethyl-1,2,4-thiadiazole to be used as a starting material. This compound and a process for its preparation are known (U.S. Pat. No. 3,260,588 (1966)).

The process for the preparation of new compounds of the formula (I) is preferably carried out using suitable solvents or diluents. Virtually all inert organic solvents are suitable solvents or diluents. These include, in particular, alcohols, such as methanol, ethanol, n- and isopropanol, n-, iso-, sec.- and tert.-butanol, ethers, such as diethyl ether, dibutyl ether, tetrahydrofuran, diglyme and dioxane, ketones, such as acetone, methyl ethyl ketone, methyl isopropyl ketone and methyl isobutyl ketone, nitriles, such as acetonitrile and propionitrile, and other highly polar solvents, dimethylformamide, dimethyl sulphoxide, sulfolane and hexamethylphosphoric acid triamide.

Virtually all acid-binding agents which can customarily be used can be employed as acid acceptors: these include, in particular, alkali metal and alkaline earth metal hydroxides or oxides, such as sodium hydroxide, potassium hydroxide and, in particular, lithium hydroxide, as well as calcium oxide or calcium hydroxide, alkali metal and alkaline earth metal carbonates, such as sodium carbonate, potassium carbonate and calcium carbonate, alkali metal alcoholates, such as sodium methylate, ethylate and tert.-butylate, and potassium methylate, ethylate and tert.-butylate, and also aliphatic, aromatic and heterocyclic amines, such as triethylamine, dimethylaniline, dimethylbenzylamine, pyridine, diazabicyclooctane and diazabicycloundecene.

The reaction temperature can be varied within a relatively wide range. In general, the reaction is carried out at between −50° and +150° C., preferably at −20° to +100° C.

The process according to the invention is carried out in general under atmospheric pressure.

In carrying out the process according to the invention, 1.0 to 1.5 mols of hydroxyacetamide of the formula (II) are employed per mol of 5-chloro-3-trichloromethyl-1,2,4-thiadiazole of the formula (III). The reaction is carried out in general in a suitable diluent, and the reaction mixture is stirred at the required temperature for several hours.

The products are isolated by customary methods: if appropriate, a part of the diluent is distilled off under reduced pressure, and the remainder of the reaction mixture is poured into water. If the products are obtained in this process in crystalline form, they are isolated by filtering them off under suction. Otherwise, the organic products are extracted with a water-immiscible solvent, such as, for example, toluene or methylene chloride; after the solution has been washed and dried, the solvent is then distilled off in vacuo from the organic phase. The products which remain are characterized by their melting point or their refractive index.

The active compounds according to the invention can be used as defoliants, desiccants, agents for destroying broad-leaved plants and germination inhibitors, and especially as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed preferably as selective herbicides in various dicotyledon crop plants, in cereals and, in particular, in rice.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs and trace nutrients such as salts of iron, manganese, boron, copper, colbat, molybdenum and zinc.

The formulations in general contain between 0.1 and 95% by weight of active compound, preferably between 0.5 and 90%.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially before the nature of the desired effect. In general, the amounts used are between 0.1 and 10 kg of active compound per ha, preferably between 0.1 and 5 kg/ha.

The examples which follow serve to illustrate the invention further.

PREPARATION EXAMPLES

EXAMPLE 1

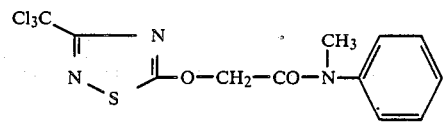

A solution of 8.4 g (0.21 mol) of sodium hydroxide in 17 ml of water is added dropwise to a stirred mixture which comprises 36 g (0.21 mol) of hydroxyacetic acid N-methylanilide, 50 g (0.21 mol) of 5-chloro-3-trichloromethyl-1,2,4-thiadiazole and 300 ml of toluene and has been cooled to $-10°$ C. The reaction mixture is stirred for 20 hours at $-10°$ C. After the mixture has been stirred with water, the organic phase is separated off, washed with water, dried and evaporated down. After the residue has been digested with ligroin, 65 g (84% of theory) of (3-trichloromethyl-1,2,4-thiadiazol-5-yl)-oxyacetic acid N-methylanilide are obtained in the form of beige-colored crystals of melting point 69° C.

EXAMPLE 2

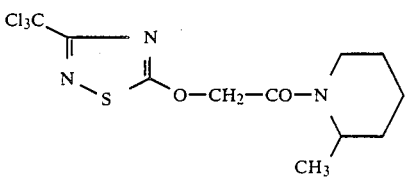

17 g (0.07 mol) of 5-chloro-3-trichloromethyl-1,2,4-thiadiazole are added to a stirred mixture which comprises 11 g (0.07 mol) of hydroxyacetic acid 2-methyl-piperidide, 4.5 g (0.07 mol) of potassium hydroxide powder and 100 ml of isopropanol and has been cooled to $-10°$ C. The reaction mixture is stirred for 20 hours at $-10°$ C. and then poured into water, and the product is filtered off under suction and washed with water. 18 g (72% of theory) of (3-trichloromethyl-1,2,4-thiadiazol-5-yl)-oxyacetic acid 2-methyl-piperidide are obtained in the form of a white powder of melting point 88° C.

The compounds of the formula (I) which are listed in Table 1 below can be obtained analogously to Examples 1 and 2:

TABLE 1

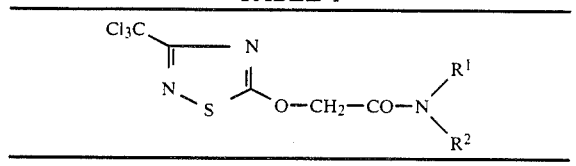

| Example No. | —N⟨R¹/R² | Melting point °C. |
|---|---|---|
| 3 | —N(CH₂—CH=CH₂)₂ | 44 |
| 4 | —N(CH₃)₂ | 88 |
| 5 | azepan-1-yl (7-membered N ring) | 115 |
| 6 | 3-methylpiperidin-1-yl | 86 |
| 7 | 4-methylpiperidin-1-yl | 76 |
| 8 | 3,5-dimethylpiperidin-1-yl | 68 |
| 9 | —N(C₂H₅)₂ | 78 |
| 10 | —N(C₂H₅)(C₆H₅) | 90 |
| 11 | —N(CH₃)(3-methylphenyl) | 77 |
| 12 | —N(CH₃)(2,3-dimethylphenyl) | 103 |
| 13 | —N(CH₃)(2-methylphenyl) | 112 |

TABLE 1-continued

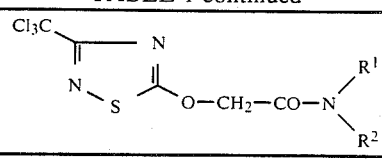

| Example No. | —N⟨R¹/R² | Melting point °C. |
|---|---|---|
| 14 | 1,2,3,4-tetrahydroquinolin-1-yl | 157 |
| 15 | 3-ethylpiperidin-1-yl | 78 |
| 16 | 2-ethylpiperidin-1-yl | 93 |
| 17 | —N(CH₃)(4-methylphenyl) | 129 |
| 18 | —N(CH₃)(2-SCH₃-phenyl) | |
| 19 | —N(CH₃)(4-SCH₃-phenyl) | |
| 20 | —N(CH₃)(3-SCH₃-phenyl) | |
| 21 | —N(CH₃)(2-CF₃-phenyl) | |
| 22 | —N(CH₃)(4-CF₃-phenyl) | |
| 23 | —N(CH₃)(3-CF₃-phenyl) | |

TABLE 1-continued

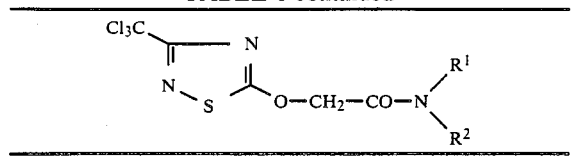

| Example No. | -N(R¹)(R²) | Melting point °C. or refractive index |
|---|---|---|
| 24 | -N(CH₃)-(2-F-C₆H₄) | |
| 25 | -N(CH₃)-(4-F-C₆H₄) | |
| 26 | -N(CH₃)-(3-F-C₆H₄) | |
| 27 | -N(CH₃)-(2,4-Cl₂-C₆H₃) | |
| 28 | -N(CH₃)-(2-NO₂-C₆H₄) | |
| 29 | -N(CH₃)-(4-NO₂-C₆H₄) | |
| 30 | -N(CH₃)-(3-NO₂-C₆H₄) | |
| 31 | -N(CH₃)-(2-SCF₃-C₆H₄) | |
| 32 | -N(CH₃)-(4-SCF₃-C₆H₄) | |
| 33 | -N(CH₃)-(3-SCF₃-C₆H₄) | |
| 34 | -N(CH₃)-(2-OCF₃-C₆H₄) | |
| 35 | -N(CH₃)-(4-OCF₃-C₆H₄) | |
| 36 | -N(CH₃)-(3-OCF₃-C₆H₄) | |
| 37 | -N(CH₃)-CH₂OCH₃ | |
| 38 | -N(CH₃)-CH₂-CF₃ | |
| 39 | -N(C₂H₅)-CH₂-CF₃ | |
| 40 | -N(CH₃)-(3,5,5-trimethylcyclohex-1-enyl) | |
| 41 | -N(CH(CH₃)₂)-C₆H₅ | |
| 42 | -N(CH₃)-(cyclohex-1-enyl) | 78 |
| 43 | -N(CH₃)-(3-Cl-C₆H₄) | 70 |
| 44 | -N(CH₃)-cyclohexyl | 57 |
| 45 | -N(C₄H₉-n)₂ | $n_D^{20}$: 1.5198 |

TABLE 1-continued

| | | |
|---|---|---|
| 46 | —N(C₃H₇—n)₂ | $n_D^{20}$: 1.5049 |
| 47 | ![structure with CH₃, N, phenyl, Cl] | 155 |
| 48 | ![structure with OCH₃, N, CH—C₂H₅, CH₃] | $n_D^{20}$: 1.5230 |

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, an excellent activity is shown by, for example, the following compounds according to the preparation examples: (1), (42), (44), (46), (48).

It will be appreciated that the instant specification and examples are set forth by way of illustration and not limitation, and that various modifications and changes may be made without departing from the spirit and scope of the present invention.

We claim:

1. A substituted 3-trichloromethyl-1,2,4-thiadiazol-5-yl-oxyacetamide of the formula

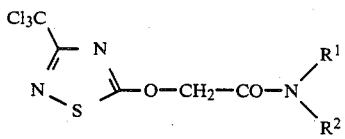

in which
R¹ and R², which can be identical or different, individually represent alkyl, cyanoalkyl, alkoxyalkyl, alkylthioalkyl, alkenyl, alkinyl or alkoxy, each having up to 10 C atoms, cycloalkyl or cycloalkenyl, each having up to 12 C atoms, aralkyl which has 1 or 2 carbon atoms in the alkyl part and 6 or 10 carbon atoms in the aryl part, and is optionally substituted by halogen, or represents aryl having 6 or 10 carbon atoms, it being possible for the aryl radical to be substituted by 1 to 3 halogen atoms, 1 to 3 alkyl or halogenoalkyl groups each having 1 to 4 carbon atoms, nitro, cyano or alkoxy having 1 to 4 carbon atoms, or wherein
the radicals R¹ and R², together with the nitrogen atom to which they are bonded, form a partially unsaturated and/or benzofused monocyclic or bicyclic structure which has up to 15 carbon atoms and is optionally substituted by 1 to 3 alkyl groups, each having 1 to 5 carbon atoms, or by two geminal alkoxy groups, each having 1 to 3 carbon atoms, or wherein
the radicals R¹ and R², together with the nitrogen atom to which they are bonded, form a saturated monocyclic structure which has up to 6 carbon atoms, is optionally substituted by 1 to 3 alkyl groups, each having 1 to 5 carbon atoms, and optionally contains in the ring a further nitrogen atom, oxygen atom or sulphur atom.

2. A compound according to claim 1, in which
R¹ represents a branched or unbranched alkyl radical with 1 to 5 carbon atoms, and
R² represents a branched or unbranched alkoxy radical with 1 to 5 carbon atoms.

3. A compound according to claim 1, wherein such compound is (3-trichloromethyl-1,2,4-thiadiazol-5-yl)-oxyacetic acid N-methylanilide of the formula

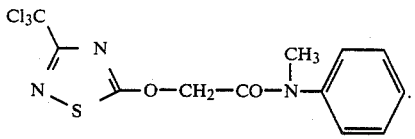

4. A compound according to claim 1, wherein such compound is (3-trichloromethyl-1,2,4-thiadiazol-5-yl)-oxyacetic acid N-methyl-N-1-cyclohexenyl-amide of the formula

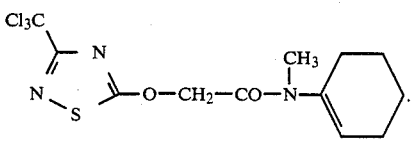

5. A compound according to claim 1, wherein such compound is (3-trichloromethyl-1,2,4-thiadiazol-5-yl)-oxyacetic acid N-methyl-N-cyclohexyl-amide of the formula

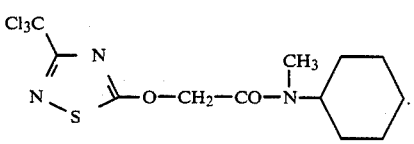

6. A compound according to claim 1, wherein such compound is (3-trichloromethyl-1,2,4-thiadiazol-5-yl)-oxyacetic acid di-n-propyl-amide

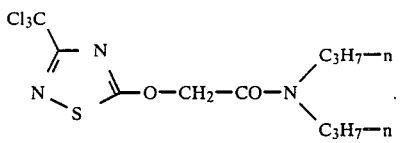

7. A compound according to claim 1, wherein such compound is (3-trichloromethyl-1,2,4-thiadiazol-5-yl)-oxyacetic acid N-methoxy-N-isobutyl amide of the formula

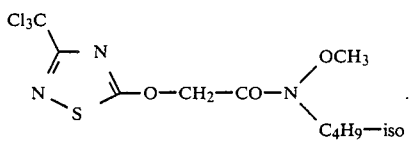

8. A herbicidal composition comprising a herbicidally effective amoint of a compound according to claim 1 in admixture with a diluent.

9. A method of combatting unwanted vegetation which comprises administering to such vegetation or to an area in which said vegetation is to be grown a herbicidally effective amount of a compound according to claim 1.

10. A method according to claim 8 wherein such compound is (3-trichloromethyl-1,2,4-thiadiazol-5-yl)-oxyacetic acid N-methylanilide, (3-trichloromethyl-1,2,4-thiadiazol-5-yl)-oxyacetic acid N-methyl-N-1-cyclohexenyl-amide, (3-trichloromethyl-1,2,4-thiadiazol-5-yl)-oxyacetic acid N-methyl-N-cyclohexyl-amide, (3-trichloromethyl-1,2,4-thiadiazol-5-yl)-oxyacetic acid di-n-propyl-amide, or (3-trichloromethyl-1,2,4-thiadiazol-5-yl)-oxyacetic acid N-methoxy-N-isobutyl amide.

11. A compound according to claim 1, in which $R^1$ represents $C_1-C_5$-alkyl, cyanoethyl, $C_1-C_4$-alkoxy-ethyl, allyl, propargyl, 1-methyl-propargyl or 1,1-dimethyl-propargyl and $R^2$ represents $C_1-C_5$-alkyl, $C_1-C_5$-alkoxy, cyanoethyl, $C_1-C_4$-alkoxy-ethyl, allyl, propargyl, 1-methyl-propargyl, 1,1-dimethylpropargyl, cyclopentyl, cyclohexyl, 3,4,6-trimethyl-cyclohexene-1-yl, benzyl, naphthyl or phenyl, which is optionally substituted by 1 to 3 radicals (methyl, chlorine, fluorine, trifluoromethyl, methoxy, methylthio, trifluoromethoxy and/or trifluoromethylthio), or wherein the radicals $R^1$ and $R^2$, together with the nitrogen atom to which they are bonded, represent pyrrolidyl, monoalkyl- or dialkyl-pyrrolidyl having 1 to 3 carbon atoms per alkyl group, morpholinyl, or dialkylmorpholinyl having 1 to 3 carbon atoms per alkyl group, piperidyl, monoalkyl-, dialkyl or trialkylpiperidyl having 1 to 3 carbon atoms per alkyl group, perhydroazepinyl (hexamethyleneimino radical), the heptamethyleneimino radical, 1,2,3,4-tetrahydroindolyl, monoalkyl- or dialkyltetrahydroindolyl having up to 3 carbon atoms per alkyl group, perhydroindolyl, monoalkyl- or dialkylperhydroindolyl having 1 to 3 carbon atoms per alkyl group, 1,2,3,4-tetrahydroquinolyl or 1,2,3,4-tetrahydro-iso-quinolyl, monoalkyl- or dialkyl-1,2,3,4-tetrahydroquinolyl or -iso-quinolyl having 1 to 3 carbon atoms per alkyl group, perhydroquinolyl or perhydro-iso-quinolyl, monoalkyl- or dialkyl-perhydroquinolyl or -perhydroisoquinolyl having 1 to 3 carbon atoms per alkyl group.

* * * * *